US009211170B2

(12) United States Patent
Gray

(10) Patent No.: US 9,211,170 B2
(45) Date of Patent: Dec. 15, 2015

(54) PROJECTILE SYRINGE SYSTEM

(71) Applicant: John M. Gray, Basking Ridge, NJ (US)

(72) Inventor: John M. Gray, Basking Ridge, NJ (US)

( * ) Notice: Subject to any disclaimer, the term of this patent is extended or adjusted under 35 U.S.C. 154(b) by 55 days.

(21) Appl. No.: 13/999,925

(22) Filed: Apr. 3, 2014

(65) Prior Publication Data

US 2015/0282914 A1 Oct. 8, 2015

(51) Int. Cl.

| | |
|---|---|
| ***A61M 5/20*** | (2006.01) |
| ***A61D 7/00*** | (2006.01) |
| ***F42B 12/54*** | (2006.01) |

(52) U.S. Cl.

CPC .. *A61D 7/00* (2013.01); *F42B 12/54* (2013.01)

(58) Field of Classification Search

CPC ........... F42B 12/54; A61D 7/00; A61M 3/00; A61M 5/178; A61M 5/2033; A61M 2005/3115; A61M 2005/3117; A61M 2005/3118; A61M 5/2053; A61M 5/20; F41B 11/85

See application file for complete search history.

(56) References Cited

U.S. PATENT DOCUMENTS

| | | | |
|---|---|---|---|
| 4,106,770 A | 8/1978 | Gray | 473/581 |
| 4,243,036 A | 1/1981 | Ott | 604/130 |
| 5,202,533 A | 4/1993 | Vandersteen | 102/512 |
| 5,607,395 A | 3/1997 | Ragsdale et al. | 604/130 |

*Primary Examiner* — Nicholas Lucchesi
*Assistant Examiner* — Morgan Lee
(74) *Attorney, Agent, or Firm* — Ernest D. Buff & Associates, LLC; Ernest D. Buff; Dave Narasimham

(57) ABSTRACT

A projectile syringe has a barrel, a spring loaded power assembly with an attached plunger, a notched plunger shaft terminating in a knob and a breach plug secured to the barrel. The spring loaded power assembly has a cylindrical sleeve with four dissected fingers, two projections on the sleeve's outer cylindrical surface securing a compressed compression spring. A cylindrical weight is captured within the sleeve by four fingers. The user attaches a needle and draws a desired amount medicament. The plunger shaft is broken flush against the breech plug. The user attaches a stabilizing tail to the breech plug end and the projectile syringe is aimed at a target animal. Stopping the syringe displaces the cylindrical weight, allowing the four fingers to displace. The proximal projections move inward, allowing the compressed compression spring to expand to the fixed breech plug, pushing the piston to deliver medicament to the animal.

7 Claims, 3 Drawing Sheets

PROJECTILE SYRINGE SYSTEM

1. FIELD OF THE INVENTION

The present invention relates to a method and device for remote injection of fluids; and, more particularly, to an injection syringe that may be easily loaded with selected amount of injectable drugs or tranquilizers according to the size of a targeted animal and delivered using a gun or other delivery mechanism.

2. DESCRIPTION OF THE PRIOR ART

Numerous prior art patents and disclosures relate to injectable syringes that may be projected towards an animal. The amount of injectable drugs or tranquilizers is fixed according to the size of the injection syringe chosen and this amount may not be selected according to the type and size of the animal.

U.S. Pat. No. 4,106,770 to John M. Gray discloses a hypodermic syringe projectile. This hypodermic syringe projectile is characterized by a hollow housing which receives an axially movable body member. A chamber for receiving treatment liquid is defined between an end of the body member and an end of the housing, which mounts an injection needle. The body member is retained in a fully retracted or filled position by flexible fingers on a wall thereof, which selectively engage an end of the housing and are maintained in such retained position by a weight. Upon impact of the syringe with an animal, movement of the weight releases the body member for movement from the retained position and a compression spring forces the treatment liquid from the chamber through the injection needle. The fingers (17b) keep the plunger in full position, the projectile requires the barrel to be completely filled with medicament and the user cannot choose how much medicament to use based on the size or weight of the animal being targeted. The plunger is driven by the drive spring (21) once the fingers (17) are allowed to release by the movement of the weight (24). The spring in the device is a compressed spring that is released by the inertial movement of a light weight.

U.S. Pat. No. 4,243,036 to Ott discloses an automatic injecting projectile. This automatically acting injecting projectile, which may be fired from a rifle or handgun for anesthesia or drug treatment of animals, consists of a casing (9) on one end of which there is a plastic extension (10) and on the other a hollow needle (5). Gas propellant may be filled into pressure chamber (15) of the casing through a check valve (1) and channel (12). Upon impact of the injecting projectile in the body of the animal deformable projectile brake (7) is pushed back and jams on a stopping cone (6). At the same time outlet (5a) of hollow needle (5) is cleared by the moving sliding sleeve (8). Thus, piston (2) may be driven by the gas propellant, thereby injecting the drug contained in drug chamber (14) and the hollow needle into the surrounding tissue of the animal through outlet (5a). Charging with the drug before firing is carried out by puncturing a silicon caoutchouc seal (3) with a hypodermic needle through a puncture opening (4) in casing (9), and then injecting the drug into drug chamber (14). After the hypodermic needle is withdrawn the silicon caoutchouc seal (3) will produce a tight seal again. The projectile has two chambers one below the other, the upper chamber having pressurized gas and lower chamber having the medicament. The medicament is discharged by pushing the piston (plunger) using gas pressure not by a compression spring that is released by the inertial movement of a light weight.

U.S. Pat. No. 5,202,533 to Vandersteen discloses a drug injection apparatus for an animal. This remotely operated injection device comprises a barrel with a piston slideable within the barrel from an initial retracted position at one end of the barrel forwardly toward the opposed end of the barrel to discharge liquid in an injection action through a needle at the forward end of the barrel. A piston slidable longitudinally within the barrel from a retracted position within which a liquid to be injected is introduced into the barrel. A spring biases the piston into the forward dispensing position in which the forward end of the piston is moved forwardly to force the liquid through the needle assembly for injecting into the animal. The release of the piston to this liquid dispensing position means is in response to a forward axial force on the release means which comprises a first portion attached to the barrel and held against movement and a second portion connected to the piston so as to be movable longitudinally therewith. The second portion is shaped to pass through said first portion, which includes an annular O-ring which is formed of a resilient material such that the O-ring can be deformed to allow passage of said second portion through said first portion when an axial force thereon exceeds a predetermined maximum force. Adjusting means are provided to vary the force at which the annular O-ring moves in a radial direction. The release of the liquid is triggered by the sudden stopping of the drug injection apparatus when the needle contacts the animal. The apparatus has two members with an O-ring in each; one fixed to the barrel and the other being movable. In the retracted position, the movable member is held in place by a compressed spring. When the drug injection apparatus hits a target animal, the O ring of the movable member passes through the aperture of the fixed member discharging the liquid. The compressed spring only biases the piston or plunger. Moreover, the device disclosed by the '533 patent can only be delivered by a shaft (i.e. an arrow, cross bow, bolt or pole).

U.S. Pat. No. 5,607,395 to Ragdale et al. discloses a device for remote injection of animals. This device is for humane injection of fluid into animals from a distance. The device comprises a hollow body with a primary chamber suitable for holding the fluid to be injected, a hollow needle at the forward end of the hollow body. The device may be projected toward the target animal by any of several conventional methods, including compressed gas or chemical explosion gun. Upon impact with the target animal a trigger mechanism, which comprises a ball and valve seat check valve, is tripped; this allows a spring to force the fluid through the needle and into the animal. The complex check valve system contains air space which, when charged with the injection liquid, results in air inside the drug chamber. No mechanism is disclosed by the '395 patent for purging this air prior to injection.

Internet Publication Teledart at discloses dart syringes for pistols and guns. Disclosed therein is a two-chamber device that has one chamber for air pressure and one chamber for the medicament or drug. The Teledart is available in various syringe sizes that accommodate different drug amounts. The amount of medicament or drug is fixed by the size of syringe chosen. The needle has a side port, which is covered by a sliding collar. Upon impact with the animal, the movement of the needle into the skin pushes the collar back from the port allowing the expanding gas to move the piston forward, injecting the fluid.

At the present time (2014), there is no truly inexpensive disposable projectile syringe. There are no major corporations manufacturing projectile syringe. None of the presently manufactured syringes have variable volume. All present projectile syringes are manufactured by small sized industries producing only specialized parts. None of the syringes can be readily filled immediately after receipt from the factory without need of multitudinous assembly procedures. World wide, at least 8 manufacturers are marketing inefficient syringes.

For example, Cap-Chur, 421 Tidwell Rd., Powder Springs, Ga. 30127 uses machined aluminum parts providing fixed volume injectable .5 caliber syringe is propelled by 50 caliber explosive charge and is reusable. Pneu-dart, 15223 Rte. 87 Highway, Williamsport, Pa. 17701 produces a .5 caliber (US) projectile syringe using plastic and aluminum parts providing fixed volume and fixed needle sizes. This one time use syringe injects using an explosive charge. TeleDart, Oatinger Strasse, 8. 67368 Westheim, Germany, discussed above, is a German 13 mm projectile syringe uses plastic components with fixed volume of injectable medicament using any needle. The injection is by compressed air and the projectile syringe can be reused. Dist Inject, Oatinger Strasse 10, CH-4057 Basel, Switzerland uses nylon parts with any needle delivers by compressed air a fixed volume of medicament. This projectile syringe is reusable. Dan Inject from Denmark uses a 13 mm projectile syringe made from plastic components using any needle and the injection of a fixed volume of medicament is by compressed air and is reusable. Paxarms 37, Rowhai St., Highfield, Timaru, Canerbury, NZ produces 13 mm fixed volume plastic projectile syringes delivering medicament by compressed air using any needle. Most of the projectile syringes available today that claim to be reusable cannot be disassembled for cleaning. None of the projectile syringes available today come to the user in a sterile condition.

Based on the foregoing, there exists a need in the art for an inexpensive single use projectile syringe system that is ready to use, sterile, and draws a selected amount of medicament or tranquilizer into the barrel of the syringe that is appropriate for the size and type of animal being targeted.

SUMMARY OF THE INVENTION

The present invention provides a method and device wherein a single use injection syringe can be loaded with a variable amount of injectable drugs or tranquilizers according to the size of a targeted animal. The injection syringe is manufactured with the following components: a) an extended needle receiving portion so that when the needle enters the animal on impact from a blow gun, spring powered, gas powered, or explosive powered gun, the needle retainer at the rear end of the needle does not penetrate the skin of the animal; b) the medicament expelling rubber plunger connected to a plunger shaft with a plurality of notches at regular intervals so that the shaft can be broken off after a desired amount of the medicament is drawn into the syringe; c) a spring loaded power assembly that has a cylindrical sleeve with a central aperture, the cylindrical sleeve being secured to the rubber plunger and having four fingers on the proximal end; d) the exterior of the cylindrical sleeve having two annular projections, a first projection at the proximal end directly above the four fingers and a second projection at the distal end; e) a compressed compression spring held between said projections; f) a slidable cylindrical weight inserted within said central aperture of the cylindrical sleeve resting at the proximal end and being gripped by the four fingers; g) the slidable weight experiencing sudden loss in velocity when the projectile syringe impacts an animal, and being thereby caused to move towards the needle by inertial forces that allows the four fingers to be depressed by the compression spring towards the center of the cylindrical sleeve, depressing the proximal end projection to release and allow the expansion of the compressed compression spring to its full length; h) said expanded compression spring having a length 1.2 to 1.5 times the length of the barrel of the injection syringe, the expanded compression spring pushing against a breech plug securely inserted at the proximal end of the injection barrel, and the proximal end being distal from the needle; i) said expanded spring pushing the plunger towards the needle to thereby release the medicament or tranquilizer into the body of the animal that has been targeted.

This projectile syringe system is inexpensive, reliable and is easy to operate since the syringe comes as a prepackaged sterile syringe with a stabilizing tail. All that the user needs to do is to attach a needle of the desired gauge and length, immerse the needle in the medicament or tranquilizer and pull the knob at the rear end of the syringe to load the exact amount of medicament needed for the size and type of the targeted animal. Upon loading the syringe with the desired amount of medicament, the user breaks the plunger shaft off at the breech plug, causing the shaft to become flush with the breach plug. The breach plug has an extension that allows the breach plug to be securely attached to the stabilizing tail. The projectile syringe with the stabilizing tail has a smooth surface and is suited for loading a blowgun, spring powered, gas powered, or explosive powered gun.

The construction detail of the projectile syringe is detailed below. The syringe has a barrel, a rubber plunger attached to a shaft through a bulbous projection in the shaft. The distal end of the spring loaded power assembly has projections that secure to outer surface projections of the plunger, thereby securing the spring loaded power assembly against the plunger and preventing its movement along the plunger shaft. The needle receiving portion of the projectile syringe is provided with an extension at the distal end of the barrel designed to accept an injecting needle. This extension at the needle-receiving end prevents the needle attachment portion from entering the skin of the animal being targeted. The spring loaded power assembly is created as a separate freestanding assembly. The spring loaded power assembly comprises a cylindrical sleeve having a central aperture slightly larger than the outer diameter of a slidable cylindrical weight, an inertia element, which is designed to be captured by four fingers provided at the proximal end of the cylindrical shell. The exterior cylindrical surface of the cylindrical sleeve has two annular projections, one projection being located at the proximal end directly above the four fingers and one projection being located at the distal end. A compressed compression spring is held between the two projections. When the slidable cylindrical weight moves towards the needle by the rapid deceleration of the syringe as the syringe hits a target animal, the fingers at the proximal end of the cylindrical sleeve are forced inwards toward the center of the cylindrical sleeve by the compression spring. The proximal projection moving inward as a part of the fingers releases the compression spring to its full length, which is 1.2 to 1.5 times the length of the barrel of the projectile syringe. The proximal end of the extended spring pushes against the breech plug, which is secured to the proximal end of the injection barrel and the piston is pushed by the compression spring towards the needle, expelling the medication or tranquilizer contained within the barrel into the body of targeted animal. The spring loaded power assembly is a fully assembled structure. In this condition, the spring loaded power assembly can be readily handled without releasing the compressed compression spring.

Briefly stated, the projectile syringe system comprises an injection syringe appointed for use in guns for the control of animals. The injection syringe can draw any amount of medicament or tranquilizer selected by the user; and the amount of medicament drawn is visible to the user on a scale printed on the barrel of the projectile injection syringe. The user snaps off the plunger shaft at the breech plug, which is secured at the proximal end of the projectile injection syringe, and attaches a stabilizing tail. The projectile injection syringe is then ready to be inserted in the barrel of a gas or explosion powered gun for targeting an animal.

In its preferred embodiment, the projectile syringe system of the present invention comprises:

a) a special syringe with an extended needle receiving portion, so that when the needle enters the animal on impact the rear needle attachment feature does not penetrate the skin of the animal;

b) a plunger shaft that connects to the medicament expelling plunger and has a plurality of notches at regular intervals so that the shaft can be broken off after a desired amount of the medicament of tranquilizer is drawn into the syringe;

c) a spring loaded power assembly being secured to the rubber plunger;

c) a spring loaded power assembly having a cylindrical sleeve with a central aperture, the exterior of which carries a compressed compression spring held between two projections, a first projection being at the proximal end, the cylindrical sleeve being dissected from the proximate end to form four fingers extending about three quarter of the length of the cylindrical sleeve;

d) a compressed compression spring held between said projections;

e) a slidable cylindrical weight inserted within said central aperture of the cylindrical sleeve resting at the proximal end gripped by the four fingers;

f) the slidable weight experiencing sudden loss in velocity when the projectile syringe impacts an animal, and being thereby moved towards the needle by inertial forces, allows the four fingers to be depressed towards the center of cylindrical sleeve depressing the proximal end projection and thereby releasing and allowing the compressed compression spring to expand to its full length;

g) said expanded compression spring having a length 1.2 to 1.5 times the length of the barrel of the injection syringe, the expanded compression spring pushing against a breech plug securely inserted at the proximal end of the injection barrel; and h) said expanded spring pushing the plunger towards the needle located at the distal end of the injection barrel, thereby releasing the medicament or tranquilizer into the body of the animal that has been targeted.

In its preferred embodiment, the method of manufacturing a projectile injection syringe of the present invention comprises the steps of:

1) manufacturing an injection syringe having an extension provided at the location where the injection needle is attached;

2) said injection syringe having a barrel for filling the medicament, a rubber plunger for drawing and expelling the medication, a shaft attached to said plunger with a pull knob at its proximal end;

3) said shaft having a plurality of notches for breaking the shaft at the end of the breach plug when sufficient amount of medicament is drawn;

4) the breech plug with the central aperture sized to pass the plunger shaft freely being first inserted from the distal end and followed by the spring loaded power assembly secured by said rubber plunger to form a shaft assembly;

5) said shaft assembly being inserted into the proximal end of the injection tube barrel and the breech plug being securely attached to the proximal end of the injection syringe barrel; whereby the projectile injection syringe is manufactured and shipped for sale in a sterile package with a firing tail suited for attachment to the breech plug.

Significant advantages are realized by practice of the present invention. This projectile syringe system is inexpensive, reliable, and easy to operate since the syringe comes in a sterile prepackaged element. All that the user needs to do is to attach the needle of choice, immerse the needle in the medicament or tranquilizer and pull the knob at the rear end of the syringe to load the exact amount of medicament or tranquilizer needed, based on the size of the animal being targeted. At this time, the user breaks the shaft attached to the plunger and the shaft now is flush at the breach plug. The breach plug has a projection that allows a stabilizing tail to be securely attached with a gas sealing flair on the distal end. This final shape of the projectile syringe has a smooth surface and is ready to fire from a gas or explosive gun.

At the present time, there is no truly inexpensive disposable projectile syringe. There are no major corporations manufacturing projectile syringes. All present projectile syringes are manufactured by small sized industries producing only specialized parts. None of the manufactured syringes have variable volume. None of the syringes can be readily filled immediately after receipt from the factory without need of multitudinous assembly procedures. Worldwide, at least 8 manufactures are marketing inefficient syringes. The projectile syringe of the subject invention will eclipse the vast majority of projectile syringes manufactured today. The projectile syringe of the subject invention can be used in virtually all existing delivery systems (including guns and blow pipes). The projectile syringe can be manufactured on standard injection molding machines. The projectile syringe can be packaged, sterilized, shipped, warehoused and marketed in the same manner as any disposable syringe. The projectile syringe has an enormous worldwide market. Anyone who uses a conventional projectile syringe presently has the necessary delivery system (gun, blow pipe, bow, cross bow etc.) but will welcome the projectile syringe of the present invention for over 90% of their needs, owing to its economy, reliability and ease of use.

BRIEF DESCRIPTION OF THE DRAWING

The invention will be more fully understood and further advantages will become apparent when reference is had to the following detailed description of the preferred embodiments of the invention and the accompanying drawing, in which.

DETAILED DESCRIPTION OF THE INVENTION

Figure 1A:
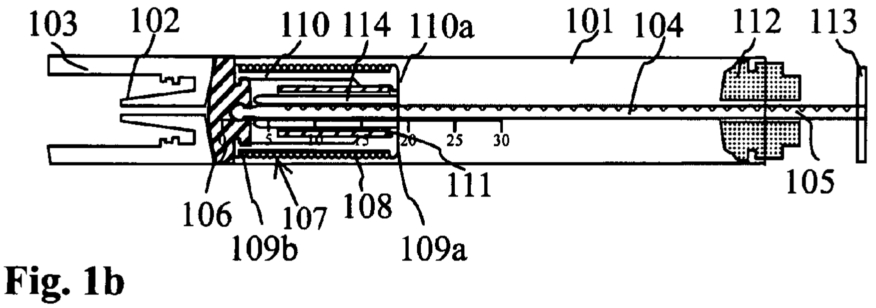
FIGS. 1*a*-1*d* illustrate the method of using the projectile syringe as it received by the customer from the manufacturing facility.

The objective of the invention is to create an inexpensive projectile syringe capable of receiving a variable quantity of medicament, as selected by the user. This feature is absent in prior art disclosures. The drive to push the plunger is not accomplished by compressed air, compressed gas or explosive charges pushing on the plunger, but rather by a compression spring that pushes against the plunger to thereby effect release of the medicament. The release of the compressed compression spring is accomplished by lateral movement of a lightweight, slidable cylindrical member.

This invention relates to a method and apparatus wherein an injection syringe may be loaded with injectable drugs or tranquilizers according to the size of animal targeted. The injection syringe is manufactured with the following key components: a) a special syringe with an extended needle receiving portion, arranged so that when the needle enters the animal on impact from a gas powered or explosive powered gun, the rear retainer of the needle does not penetrate the skin of the animal; b) the plunger shaft of the injection syringe that connects to the medicament expelling plunger has a plurality of notches at regular intervals so that the shaft can be broken off after a desired amount of the medicament or tranquilizer is drawn into the syringe; c) a spring loaded power assembly having a cylindrical sleeve, the exterior of which carries a compressed compression spring held between two projections one at the proximal end and one at the distal end and having a central aperture, the cylindrical sleeve being dissected from the proximate end forming four fingers for about three quarters of the length of the cylindrical sleeve; d) a slidable cylindrical weight with a central aperture suitable for the free movement of the plunger shaft, the weight being held within the cylindrical sleeve aperture resting against interior projections and having a close fitting tolerance between the outer surface of the cylindrical weight and central aperture of the cylindrical sleeve, thereby holding the proximal end of the cylindrical sleeve and fingers, allowing the proximal end projections to thus secure the compressed compression spring at the proximal end; e) the slidable weight being adapted to maintain its velocity when the projectile syringe impacts an animal, whereupon the slidable weight moves towards the needle by inertial forces, releasing the proximal end finger's projection towards the interior of the cylindrical sleeve, thus releasing and allowing the compressed compression spring wound on the outer surface of the cylindrical sleeve to expand to its full length; f) the compression spring having a length greater than the overall length of the barrel of the injection syringe, typically 1.2 to 1.5 times the barrel length, so that when allowed to expand the compression spring pushes against a breech plug inserted at the proximal end of the barrel; g) said expanded spring pushing the plunger towards the needle to thereby release the medicament or tranquilizer into the body of the animal that has been targeted.

The method of manufacturing the projectile syringe is detailed below. First, the spring loaded power assembly is created as a separate assembly. The spring loaded power assembly comprises a cylindrical sleeve having a central aperture the interior diameter of which is substantially larger than the outside diameter of a slidable cylindrical weight that operates as an inertia element designed to rest against interior projections of the cylindrical sleeve which are substantially identical to the outer diameter of the weight. The cylindrical weight has a central aperture that is slightly larger than the plunger shaft of the injection syringe. The cylindrical sleeve has external projections at the proximal end and distal end to retain a compressed compression spring on the external cylindrical surface of the cylindrical sleeve. The proximal end of the cylindrical sleeve is dissected into four fingers. The projections have substantially identical outer diameters operative to secure the compression spring at the proximal end when the close fitting slidable cylindrical weight is inserted within the central aperture of the cylindrical sleeve's interior projections.

Assembly of the projectile syringe comprises the following steps. First, the compressed compression spring is slid over the cylindrical outer surface fingers resting against the distal projection of the cylindrical sleeve. Now the compression spring is compressed and the slidable cylindrical weight is inserted through the central aperture of the cylindrical sleeve until the proximal projection on the outer surface of the cylindrical shell secures the compression spring in its compressed state.

The plunger shaft has a large diameter pull knob or handle at its proximal end and has many notches made at equal distances for easily breaking the shaft after withdrawing the exact amount of medicament needed. A breech plug having a central aperture to pass the plunger shaft is created with close fitting tolerance and a small external projection at its distal end for securing the breech plug within the proximal end of the barrel of the injection syringe's interior projection. First the breach plug is slid over the distal end of the plunger shaft. The spring loaded power assembly is attached to the rubber plunger slid over the distal end of the plunger shaft and the distal projection on the shaft is inserted into the rubber plunger. The whole assembly is inserted into the barrel of the injection syringe from its proximal end. The breach plug is secured against proximal end opening of the injection barrel. The prepared projectile injection syringe is ready to be shipped to the customer and does not have any medicament or tranquilizer within the barrel.

The user takes the prepared projection injection syringe from the package and attaches the required size needle according to the size of animal targeted. The user then sticks the needle in the medicament vial in the usual manner and draws the desired amount of medicament into the syringe tube by pulling on the plunger shaft knob. The amount of medicament drawn is clearly visible on a scale printed on the barrel of the injection syringe. The plunger shaft is broken off, at which point the proximal end of the plunger shaft is flush with the proximal end of the breach plug. Now the user attaches the firing tail to the breech plug using the projection provided. The projectile injection syringe has smooth surfaces with a gas seal and is ready to be inserted into the barrel of a projecting device of choice.

FIG. 1*a* illustrates the projectile syringe in the 'as manufactured' condition. The projectile syringe is typically received by a customer in the 'as manufactured' condition. The barrel of the injection syringe is shown at 101. The needle attachment end 102 has an extended portion 103 to prevent a needle retaining end from penetrating the body of the animal. The shaft 104 has a plurality of notches 105 and connects to a plunger 106. A spring loaded power assembly is shown at 107, which is secured to rubber plunger 106 preventing its lateral sliding motion. The spring loaded power assembly has a compressed compression spring 108 held between a proximal projection 109*a* and a distal projection 109*b* on a cylindrical shell 110. The proximal end of cylindrical shell 110 is dissected into four fingers as shown at 110*a* and the dissection cut extends about three quarter the length of the cylindrical shell. The cut portion is marked 114. The projection at 109*a* is inclined so that the compressed compression spring exerts an inward force against the projection. The plunger 106 attaches to the distal end of the spring loaded power assembly 107, as shown. A slidable cylindrical weight 111 supports and holds the proximal projection 109*a*. The proximal end of the barrel 101 attaches to the breech plug 112. The pull knob is shown at 113.

Figure 1B:
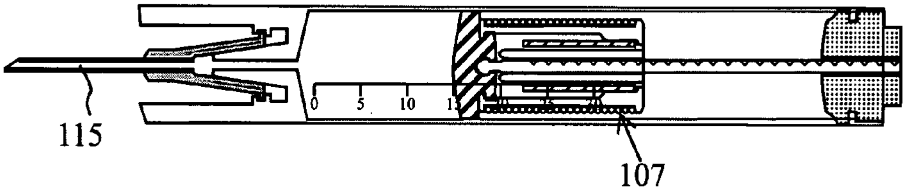

FIG. 1*b* illustrates the projectile syringe with needle 115 attached typically as a twist lock mechanism. The needle is inserted in the medicament or tranquilizer and the pull knob 113 is pulled to draw the medicament into the barrel 101 of the projectile syringe. The plunger shaft 104 is snapped or broken at the breech plug 112 as shown.

Figure 1C:
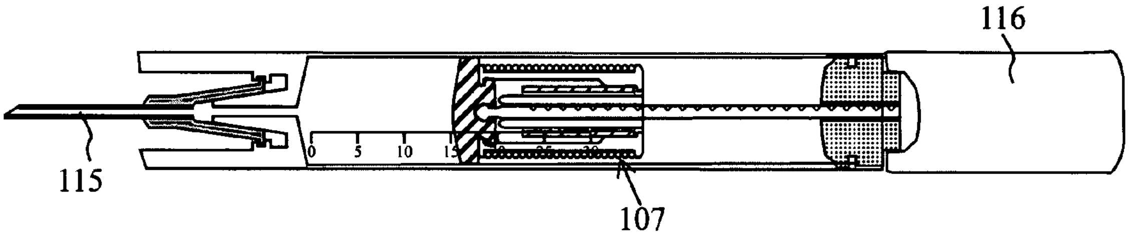

FIG. 1*c* illustrates the projectile syringe of FIG. 1*b* with the stabilizing tail 116 attached.

Figure 1D:
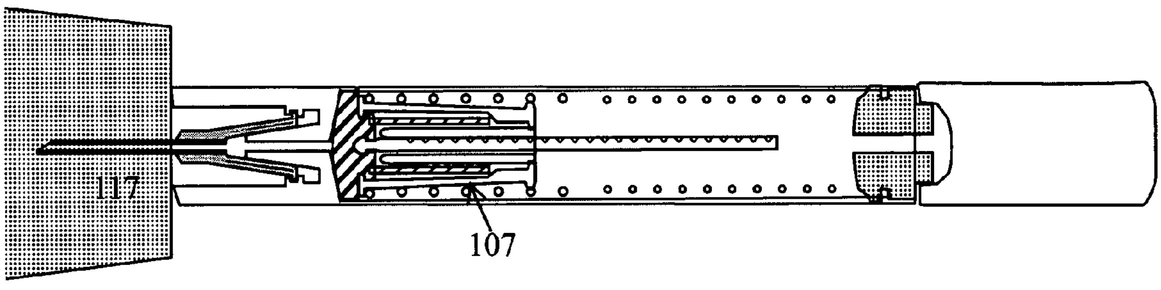

FIG. 1*d* illustrates the projectile syringe of FIG. 1*c* when fired from a gun so that the needle 115 penetrates the body of the target animal 117. The sudden stopping of the projectile syringe on impact with target animal causes the slidable cylindrical weight to move towards the needle, as shown. This movement causes the proximal end projection 109*a* to depress towards the center of the barrel; loss of support provided by the slidable cylindrical weight releases the compression spring 108, which has length 1.2 to 1.5 times the overall length of the barrel. The expanded compression spring pushes against the non-moving breech plug 112 and therefore pushes the plunger 106 towards the needle 115 releasing the medication from the projectile syringe barrel 101. These referenced indicia in FIG. 1*a* are applicable to each of FIGS. 2*a* through 3*e*, and are not repeated for clarity.

Figure 2A:
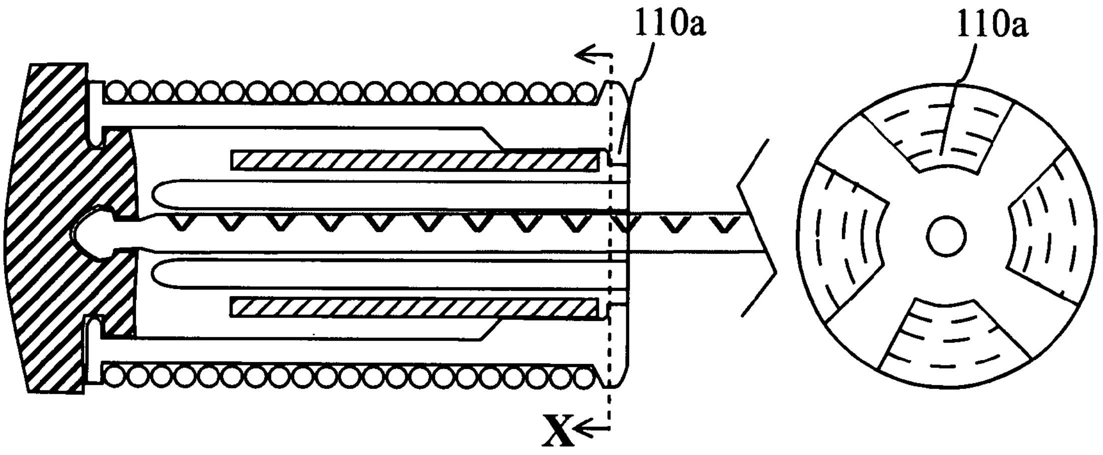
FIG. 2*a* illustrates the front view and section view at XX of the spring loaded power assembly of the projectile syringe system.

FIG. 2*a* illustrates an elevation view and a cross sectional end view at XX of the spring loaded power assembly. The spring loaded power assembly of the projectile syringe is shown in the condition it is typically received from the factory. This figure shows the position of the four fingers 110*a* at the proximal end of the cylindrical shell 110, which operate to the projection at 109*a* when the slidable cylindrical weight 111 is inserted. The compressed compression spring 108 is held between 109*a* and 109*b*.

Figure 2B:
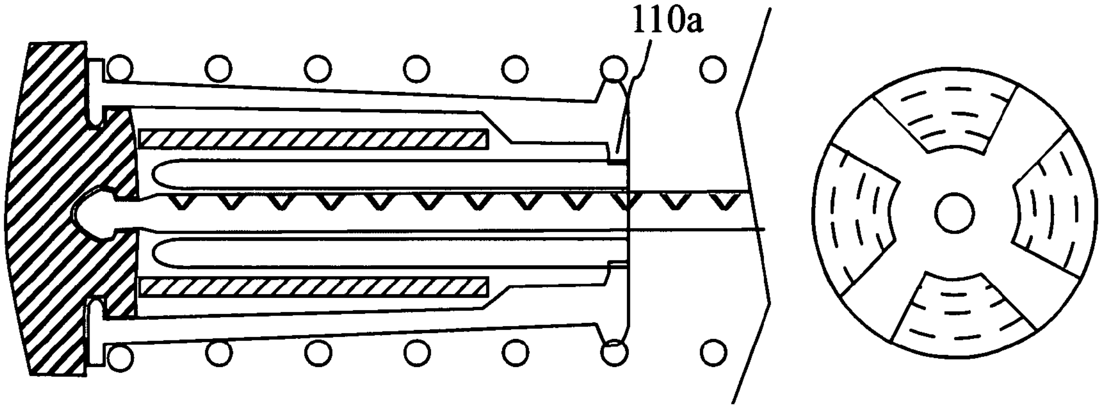
FIG. 2*b* illustrates the front view and side view of the spring loaded power assembly after the syringe impacts a target animal showing the four fingers forced towards the interior of the cylindrical shell and the compression spring released.

FIG. 2*b* illustrates a side view of the spring loaded power assembly of the projectile syringe after it has been fired from a gun and has impacted the skin of a target animal. The slidable cylindrical weight 111 has moved towards the needle to effect release of the four fingers 110*a* at the proximal end of the cylindrical shell 110. Movement of cylindrical weight 111 allows the depression of fingers 110*a* towards the interior of the cylindrical shell. As a result, the compressed compression spring 108 is released and expanded. The end view clearly shows smaller sized configuration of fingers 110*a* as the compressed compression spring slips out and pushes against the breech plug, thereby pushing the piston 106 towards the needle 115 to effect delivery of the medication.

Figure 3A:
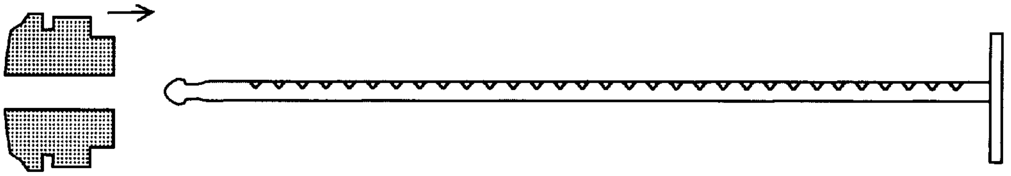
FIGS. 3*a*-3*d* illustrate certain details concerning the process for manufacturing the projectile syringe.

FIG. 3*a* illustrates the assembly process for the projectile syringe. The breach plug 112 is inserted from the distal end of the shaft as shown.

Figure 3B:
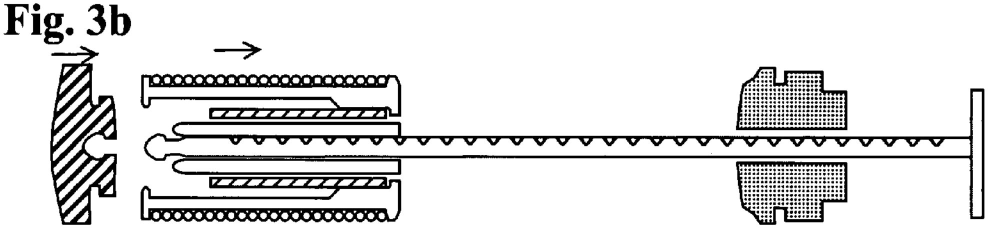

FIG. 3*b* illustrates the next step of assembly process for the projectile syringe. The spring loaded power assembly 107 is inserted from the distal end of the shaft as shown.

Figure 3C:
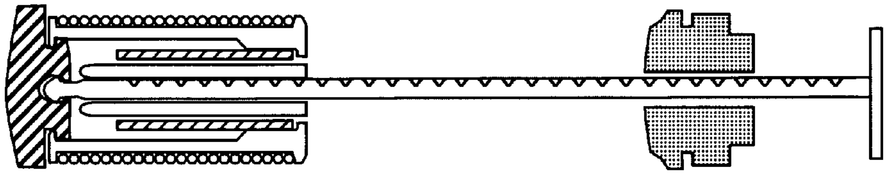

FIG. 3*c* illustrates the next step of assembly process for the projectile syringe. Next the rubber plunger is attached to the plunger shaft using the central bulb like projection of the shaft, the external lip of the plunger engaging with the distal projection of the spring loaded power assembly 107. The entire assembly is referred to herein as the ‘shaft assembly’.

Figure 3D:
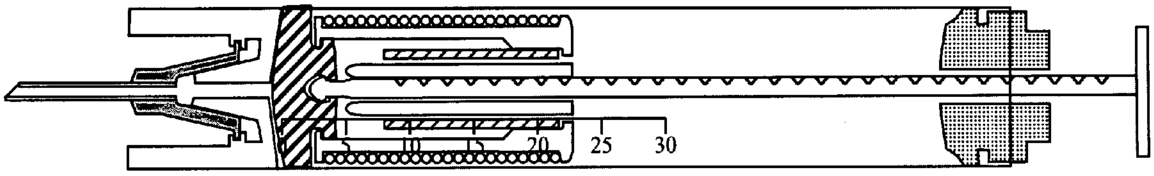

FIG. 3*d* illustrates the next step of assembly process for the projectile syringe. The ‘shaft assembly’ is inserted into the barrel 101 of the projectile injection syringe from the proximal end of the barrel. Note that the plunger external surfaces contact the inner surface of the barrel forming a liquid tight contact. The breech plug is securely attached to the barrel at the proximal end using attachment features such as a ring, notch and the like forming an unmoving breech plug. The extra clearance sliding feature of the shaft 104 through the breech plug 112 provides a vent hole preventing air lock during loading of the medicament.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A projectile syringe system, comprising:

a) a syringe appointed to be fired from a delivery gun towards a target animal for delivering injectable medicament or tranquilizer, said delivery gun comprising a spring, compressed gas or explosive fired gun;

b) said syringe having an extended needle receiving portion, so that when a needle enters the animal on impact a rear needle attachment feature does not penetrate the skin of the animal;

c) a plunger shaft of the syringe that connects to a medicament expelling plunger having a plurality of notches at regular intervals so that the shaft can be broken off, after a desired amount of the medicament is drawn into the syringe, at a breech plug location that fits securely on a proximal end of said syringe;

d) a spring loaded power assembly having a cylindrical sleeve, the exterior of which carries a compressed compression spring held between two projections, a first projection being located at a proximal end and a second projection being located at a distal end and having a central aperture, the cylindrical sleeve being dissected from a proximate end to thereby form four fingers extending about three quarters of the length of the cylindrical sleeve;

e) said plunger being secured to said spring loaded power assembly;

f) a slidable cylindrical weight with a central aperture larger than the plunger shaft diameter, the weight being held within the cylindrical sleeve aperture by four fingers having interior projections and having a close fitting tolerance between an outer surface of the cylindrical weight and said interior projections, thereby holding proximal end projections to secure the compressed compression spring at a proximal end;

g) the slidable weight being adapted to maintain substantially the same velocity as the projectile syringe prior to impact on an animal, the projectile syringe being caused to decelerate upon impact, whereupon the slidable weight is moved towards the needle by inertial forces, releasing the proximal end finger’s projection towards an interior of the cylindrical sleeve, thus releasing and allowing the compressed compression spring wound on the outer surface of the cylindrical sleeve to expand to its full length;

h) the compression spring having a length greater than the overall length of a barrel of the injection syringe, and being about 1.2 to 1.5 times the barrel length so that, upon expansion, the compression spring pushes against a breech plug inserted at a proximal end of the barrel; and i) said compression spring pushing the plunger towards the needle to thereby release the medicament or tranquilizer into the body of the animal that has been targeted.

2. The projectile syringe system as recited by claim 1, wherein said plunger is made from a rubber elastomer.

3. The projectile syringe system as recited by claim 1, wherein the said plunger shaft, barrel, and breech plug are made from a polymeric material.

4. The projectile syringe system as recited by claim 1, wherein the said barrel of the injection syringe has graduated markings indicating the amount of medicament drawn by a user.

5. The projectile syringe system as recited by claim 1, wherein said inertial forces exerted by the slidable cylindrical weight are small.

6. The projectile syringe system as recited by claim 1, wherein the compressed compression spring when released has sufficient compression to push the piston towards the needle, expelling the medicament contained in the injection syringe.

7. A method of manufacturing a projectile syringe comprising the steps of:

a) creating a spring loaded power assembly comprising;

i) a cylindrical sleeve with a central aperture and having an external cylindrical surface with two projections one at a proximal end, one at a distal end and said proximal end being dissected to form four fingers, said dissection extending about three quarters of the length of the cylindrical sleeve, measured from a proximal end;

ii) a slidable cylindrical weight inserted through the aperture of said cylindrical sleeve and captured by said four fingers at a proximal end of said cylindrical sleeve;

iii) a compressed compression spring held between the two projections on the external cylindrical surface of the cylindrical sleeve;

b) creating a plunger shaft with a bulbous end attachment feature at a distal end, said plunger shaft having a plurality of notches along its length and terminating with a pull knob at the proximal end thereof;

c) creating a rubber plunger having an external diameter sized to fit a barrel of a projectile syringe, and having an external attachment feature for securing said spring loaded power assembly and central attachment feature to attach to a plunger shaft bulbous distal end;

d) inserting a breech plug followed by the rubber plunger attached to the spring loaded assembly onto the plunger shaft from its distal end and securing the rubber plunger attached spring loaded power assembly to the bulbous attachment feature of the plunger shaft creating a shaft assembly;

e) inserting said shaft assembly into a proximal end of the barrel of the syringe and securing said breech plug at the proximal end of said barrel; whereby a projectile syringe is created and ready for shipment to a customer.

* * * * *